US007285128B1

(12) United States Patent
Danzey

(10) Patent No.: US 7,285,128 B1
(45) Date of Patent: Oct. 23, 2007

(54) LUMBAR TRACTION TABLE

(76) Inventor: William P. Danzey, 1590 U.S. 27 North, Avon Park, FL (US) 33825

(*) Notice: Subject to any disclaimer, the term of this patent is extended or adjusted under 35 U.S.C. 154(b) by 157 days.

(21) Appl. No.: 11/258,497

(22) Filed: Oct. 25, 2005

(51) Int. Cl.
*A61H 1/02* (2006.01)
*A61F 5/00* (2006.01)

(52) U.S. Cl. ......................... 606/245; 606/242; 602/32

(58) Field of Classification Search ................ 606/237, 606/240, 241, 242, 243, 244, 245; 601/23, 601/24; 602/32, 33; 128/845; 482/142; 5/612, 613, 616–618
See application file for complete search history.

(56) References Cited

U.S. PATENT DOCUMENTS 4,489,714 A * 12/1984 Barnes ....................... 606/245
4,649,905 A 3/1987 Barnes
5,022,388 A 6/1991 Harter
5,192,306 A 3/1993 Scott et al.
5,320,640 A 6/1994 Riddle et al.
5,423,861 A 6/1995 Kelley
6,102,882 A 8/2000 Cobo
6,186,968 B1 * 2/2001 Wu ............................. 602/32
6,277,141 B1 8/2001 Lake
6,328,759 B1 12/2001 Zhang
6,638,299 B2 10/2003 Cox
6,679,905 B2 1/2004 Peetros et al.

* cited by examiner

*Primary Examiner*—Quang D. Thanh
(74) *Attorney, Agent, or Firm*—Charles J. Prescott

(57) ABSTRACT

A flexion-traction type lumbar traction table for treating a patient including a base supporting a stationary head-thoracic support and a pivotally movable pelvic support section positioned end-to-end with the head-thoracic support section. Upper and lower pelvic sections form the pelvic support section and are connected together for sliding longitudinal translation of the upper pelvic section on the lower pelvic section. A proximal end of the lower pelvic section is connected for pivotal movement about a horizontal transverse flexion axis between a horizontal first position and a downwardly inclined second position. An axial traction member is pivotally connected between the upper pelvic section adjacent to a distal end thereof and the frame just beneath the flexion axis wherein said upper pelvic section is automatically slidably translated further from said proximal end of the lower pelvic section as the pelvic support section is manually pivoted downwardly for enhanced longitudinal traction.

9 Claims, 4 Drawing Sheets

LUMBAR TRACTION TABLE

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to chiropractic treatment tables of the type for generally horizontally supporting a patient in a face-down position, and more particularly to such a table with improved axial traction during flexion-distraction and lateral-distraction, or the combination of both.

2. Description of Related Art

Currently, lumbar flexion-distraction tables used by chiropractors produce a very slight longitudinal traction by pivotal displacement of the pelvic support section that occurs during flexion. The downwardly pivotal movement of the pelvic support section about a transverse horizontal axis positioned adjacent the head-thoracic support section of the table effects this slight traction. With the patient in a face-down position atop the table, the practitioner places one hand on the patient's spine for stabilization and the other hand on a traction handle connected to the pelvic support section to produce this traction as the pelvic support section is pivoted downwardly. With these conventional chiropractic treatment tables, the pelvic support section does not, and cannot slide longitudinally to enhance the traction feature.

Prior U.S. patents have tried to improve upon this basic treatment concept. U.S. Pat. No. 6,277,141 to Lake teaches an orthopedic apparatus for supporting a patient wherein the end table (16) is mounted on the support frame for sliding movement lengthwise of the apparatus. A table having a static board, a moving board, which is displaceable towards and away from the static board, and a device for applying traction force is taught by Cobo in U.S. Pat. No. 6,102,882.

A chiropractic treatment table including a longitudinally moveable head support portion is disclosed by Cox in U.S. Pat. No. 6,638,299. This type of cervical traction table does include a sliding portion for neck traction, but the longitudinal component of traction is produced by the practitioner, not the table, and is not directly linked to the amount of flexion. With this type of system, it would be difficult for the practitioner to produce the amount of lumbar longitudinal traction produced by the present invention. Also, with the Cox design, the traction handle moves away from the practitioner which would be impractical during lumbar flexion distraction as the practitioner's hands are already significantly separated.

McAfee discloses a head flexion mechanism for a chiropractic table in U.S. Pat. No. 6,436,126. Zhang teaches spinal three-dimensional orthopedic equipment in U.S. Pat. No. 6,328,759 and U.S. Pat. No. 6,679,905 to Peetros, et al. discloses a modular drop mechanism for a chiropractic table. Scott, et al. teaches a chiropractic manipulation table with flexion/distraction headpiece in U.S. Pat. No. 5,192,306.

Additional known prior art is listed herebelow:

U.S. Pat. No. 5,320,640 Riddle, et al.

U.S. Pat. No. 5,423,861 Kelley

U.S. Pat. No. 5,022,388 Harter

U.S. Pat. No. 4,649,905 Barnes

BRIEF SUMMARY OF THE INVENTION

The present invention provides several advantages for spinal treatment afforded by a chiropractic table which includes the present invention's features. This improved chiropractic table automatically produces a progressive amount of longitudinal traction as flexion is applied by the downward pivotal movement of the pelvic support section. Differential amounts of longitudinal traction may be selected by optional pivotal location of the traction bar member at the time of treatment. Moreover, the present invention, when assisted by gravity to produce enhanced longitudinal traction, allows the practitioner to produce a degree of longitudinal traction not possible with existing traction tables and by connecting the traction handle to the non-sliding lower pelvic section of the pelvic support section, the traction handle does not move away from the practitioner during flexion.

This invention is thus directed to a flexion-traction type lumbar traction table for supporting and treating a patient including a base supporting a stationary head-thoracic support and a pivotally movable pelvic support section positioned in spaced end-to-end relation to the head-thoracic support section. Upper and lower pelvic sections form the pelvic support section and are connected together for sliding longitudinal translation of the upper pelvic section on the lower pelvic section. A proximal end of the lower pelvic section is connected for pivotal movement about a horizontal transverse flexion axis between a horizontal first position and a downwardly inclined second position. An axial traction member is pivotally connected between the upper pelvic section adjacent to a distal end thereof and the frame just beneath the flexion axis wherein said upper pelvic section is automatically slidably translated further from said proximal end of the lower pelvic section as the pelvic support section is manually pivoted downwardly for enhanced longitudinal traction.

It is therefore an object of this invention to provide a flexion-type lumbar traction table which enhances and extends the amount of flexion traction that may be introduced to the patient by the practitioner during chiropractic treatment.

It is still another object of this invention to provide a selectable degree of enhanced flexion traction afforded by a lumbar traction table.

Still another object of this invention is to incorporate the present invention into flexion-distraction spinal traction tables which introduce both flexion-distraction and lateral-distraction separately or together and for producing enhanced traction extension of the spine during either or both of these treatment procedures.

Yet another object of this invention is to provide a traction handle for pivotal downward flexion-distraction patient movement which does not move away from the practitioner with increased downward pivotal movement.

In accordance with these and other objects which will become apparent hereinafter, the instant invention will now be described with reference to the accompanying drawings.

BRIEF DESCRIPTION OF THE SEVERAL VIEWS OF THE DRAWING(S)

DETAILED DESCRIPTION OF THE INVENTION

Figure 1:
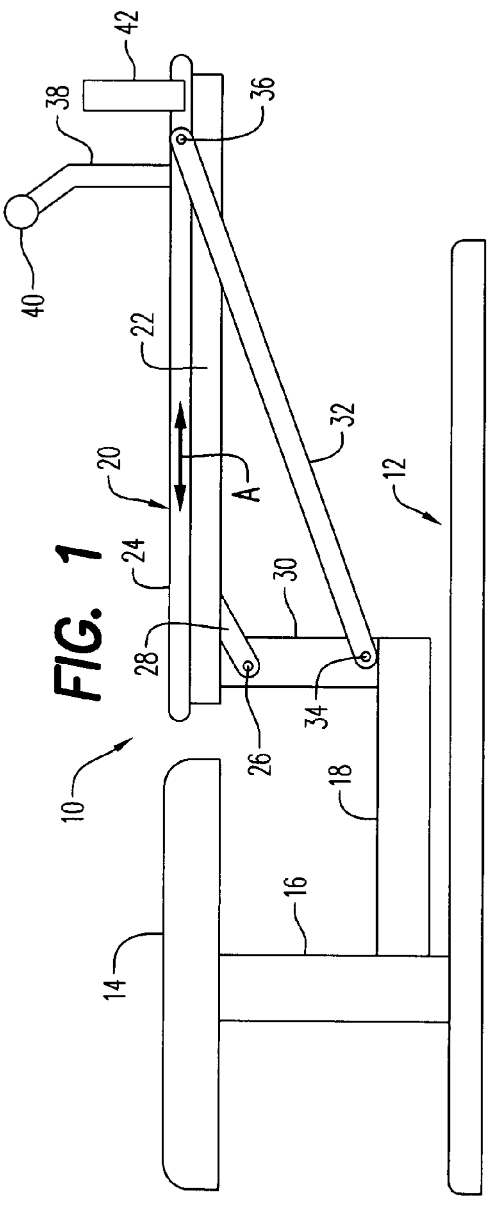
FIG. 1 is a simplified side elevation view of a flexion-traction type lumbar traction table incorporating aspects of the present invention.
Figure 2:
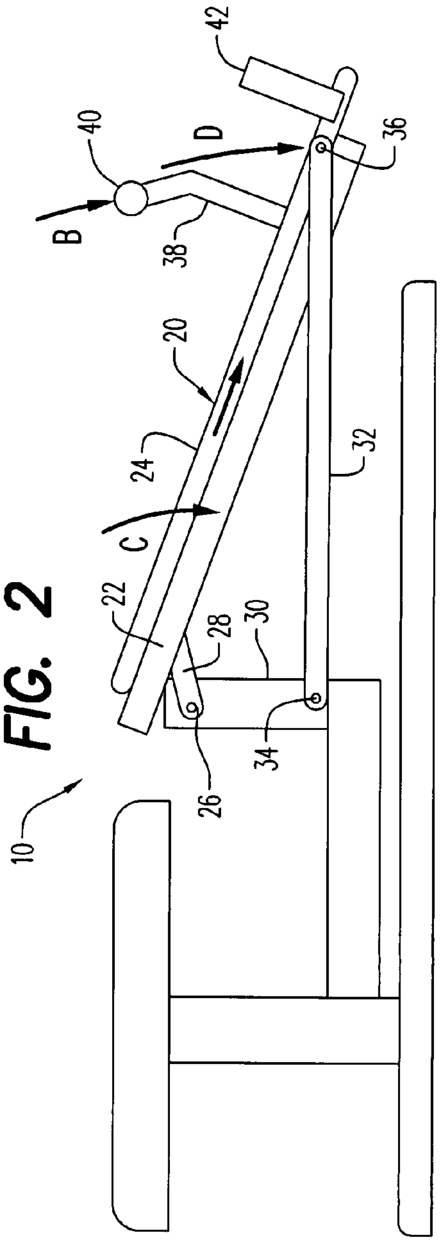
FIG. 2 is a view of FIG. 1 showing the pelvic support section pivoted downward during flexion-traction displacement.
Figure 3:
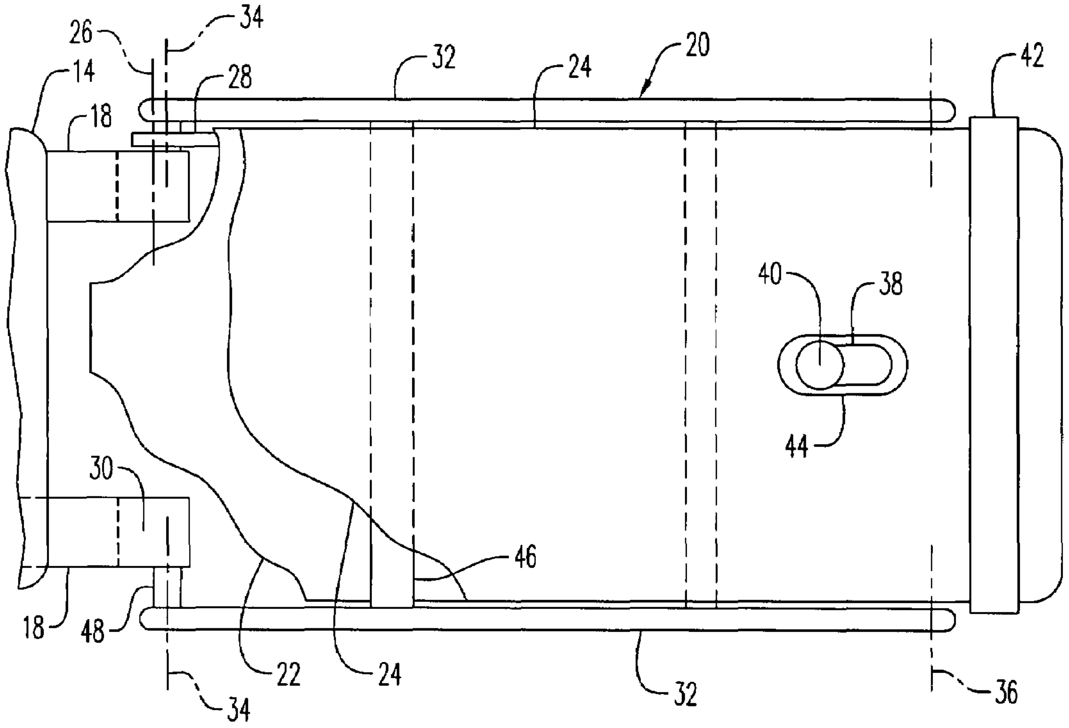
FIG. 3 is a top plan broken view of a portion of FIG. 1.

Referring now to the drawings, and firstly to FIGS. 1 to 3, one embodiment of a flexion-traction type lumbar traction table embodying aspects of the invention is there shown generally at numeral 10. This traction table 10 includes a frame 12 supportable atop a level floor surface and which includes an upright support 16 having a horizontally disposed stationary head-thoracic support section 14 connected thereatop. Two spaced longitudinally extending frame members 18 as best seen in FIG. 3 extend from the upright support 16 beyond the proximal end of the frame head-thoracic support section 14. An upwardly extending frame member 30 is supportively connected at a lower end thereof to the end of each horizontal frame member 18.

A pelvic support section 20 includes a lower pelvic section 22 and an upper pelvic section 24 which is slidably engaged for longitudinal movement only in the direction of arrow A to and atop the lower pelvic section 22. The lower pelvic section 22 is pivotally connected by rigid links 28 to each of the upright frame members 30 about a transverse flexion axis 26 positioned heightwise just below the lower pelvic section 22. An adjustable counterbalance spring (not shown) between pelvic support section 20 and upright frame member 30 to counterbalance the weight of a patient's lower torso and legs may also be provided.

Two elongated axial traction members 32 are each positioned along one longitudinal side martin of the pelvic support section 20. One end of each axial traction member 18 is pivotally connected to the edge of the upper pelvic section 24 about a first transverse horizontal pivotal axis 36 positioned adjacent to the distal end of the upper pelvic section 24. The other end of each of these axial traction members 32 is pivotally connected about a second horizontal transverse pivotal axis 34 through the lower end of the upright frame member 30. this second pivotal axis 34 is spaced beneath the flexion axis 26, the distance therebetween being selectively variable to determine the degree of enhanced sliding traction movement of the upper pelvic section 24 as will be described herebelow.

Connected to the lower pelvic section 22 is an upwardly extending traction handle 38 having an enlarged distal end 40 to facilitate hand grasping and exertion thereagainst in the direction of arrow B. With a patient in the prone position atop the traction table 10 with the torso and cervical area positioned atop the head-thoracic support section 14 and the lower torso and legs positioned atop the pelvic support section 20, and with the preferred location of the traction handle 38 being between the legs centrally positioned side-to-side of the side margins of the pelvic support section 20, a practitioner may more effectively apply pressure in the direction of arrow B causing the pelvic support section 20 to move pivotally downwardly in the direction of arrow D about the flexion axis 26. Note that this traction handle 38 does not move away from the practitioner by being connected to the lower pelvic section 22. An adjustable leg strap 42 attached to either side margin of the upper pelvic support 24 immediately adjacent the distal end thereof secures the users ankles and lower legs in position during treatment.

Figure 4:
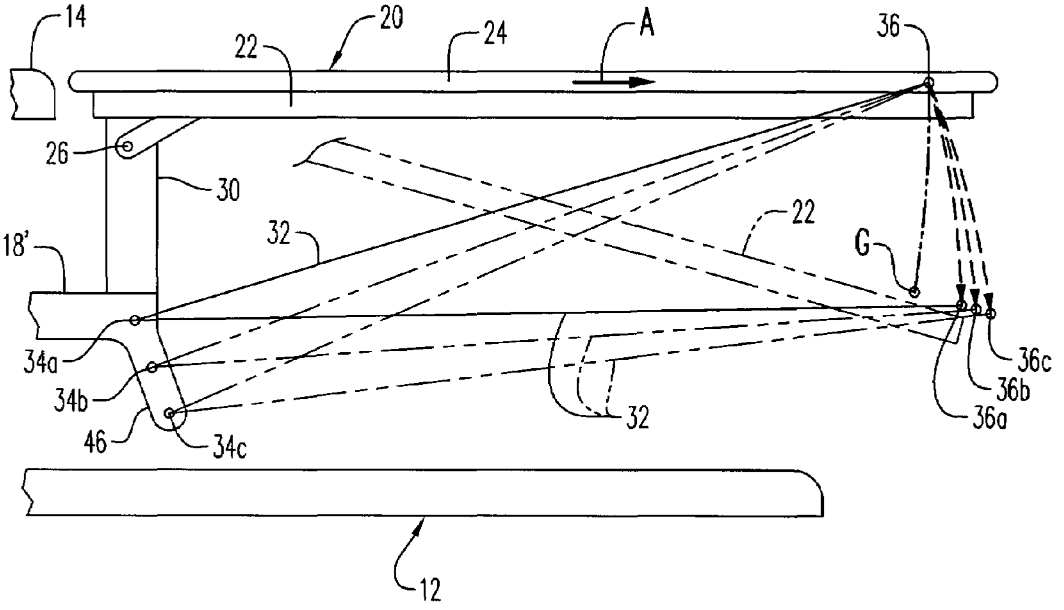
FIG. 4 is a side elevation schematic view of an alternate embodiment of the pelvic support section of FIG. 1 showing the novel adjustable geometry (shown in phantom) achieved by the invention.

Referring additionally to FIG. 4, two important aspects of the invention are there shown. The first aspect is with respect to the enhanced traction flexion movement achieved by the invention. This is depicted by reiterating that the upper pelvic section 24 is slidably connected for longitudinal translation in the direction of arrow A with respect to the lower pelvic section 22. This longitudinal translation or extending movement of the upper pelvic section 24 is accomplished by the axial traction members 32. Except for these features, the first pivotal axis 36 would pivot downwardly to point G of the pelvic support section 20. This understandably occurs when visualizing the entire pelvic support section 20 is pivotally moved in a conventional manner about the transverse flexion axis 26. However, with the axial traction members 32 being pivotally connected to the lower positioned second pivotal axis 34*a*, the first transverse axis 36 moves pivotally to 36*a* shown in phantom.

Typically, the useful longitudinal traction movement of a conventional prior pelvic support section will cause a longitudinal therapeutic extension of the lower torso of a patient of approximately 1". However, with the invention as shown in FIG. 4, the first transverse pivotal axis 36 moving to 36*a* shown in phantom, represents a longitudinal tractional extension of approximately 2.75", nearly three times the amount of longitudinal traction imposed upon a patient.

Still referring to FIG. 4, by providing a series of pivotal connections at 34*a*, 34*b* and 34*c*, the same sized axial traction members 32 this produces still further extensions of the longitudinal tractional displacement imposed upon a patient as the upper pelvic section 24 slidably moves to position the first pivotal axis at 36*a*, 36*b* or 36*c*.

Figure 5:
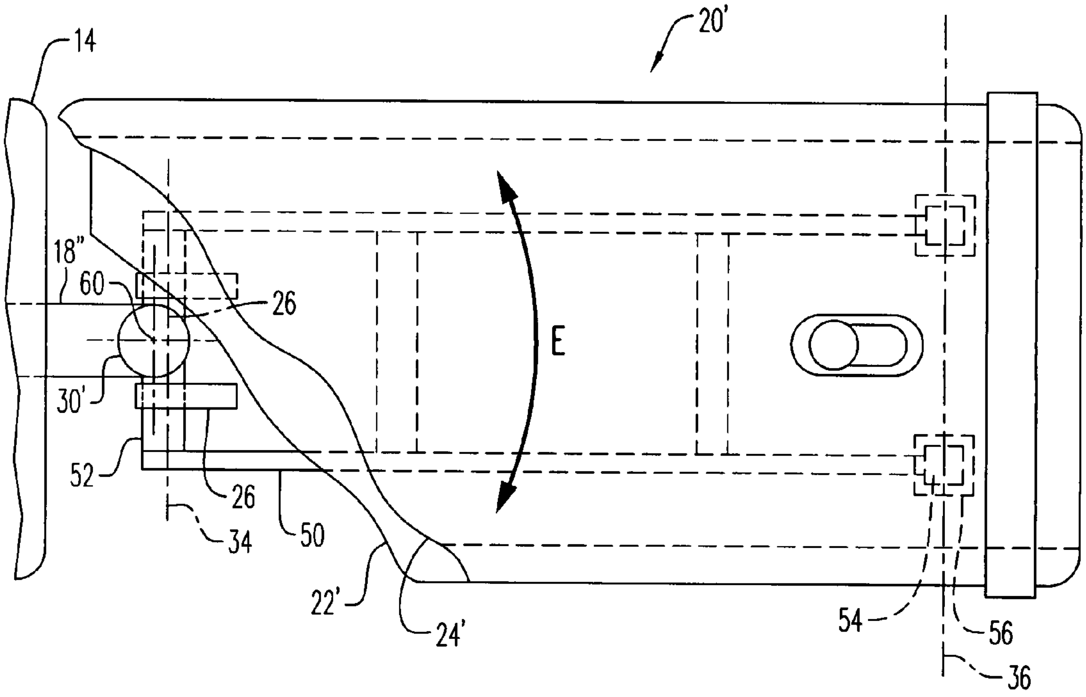
FIG. 5 is a top plan view similar to FIG. 3 of an alternate and preferred embodiment of the invention which includes aspects of rotational or lateral traction features.

Referring lastly to FIG. 5, the preferred embodiment of the improved pelvic support section is there shown at numeral 20'. The primary additional feature of this embodiment 20' is the inclusion of the lateral-distraction movement which may be introduced by a practitioner by the rotation of the entire pelvic support section 20' about the upright pivotal axis 60 of frame member 30' back and forth in the direction of arrow E. Thus, in addition to the enhanced longitudinal tractional features of this invention previously described, the practitioner may couple those benefits with the flexion-lateral distraction features provided by this embodiment 20'.

The previously described features of the positioning of the flexion axis 26 and the second pivotal axis 34 are included in this embodiment 20'. However, an axial traction member 50 formed as a somewhat ladder-type section (shown in hidden lines), has one end thereof pivotally connected to the upper pelvic section 24' about the first pivotal axis 36 through enlarged sleeves 54 while the opposite end of this axial traction member 50 is pivotally connected about the second pivotal axis 34 through elongated sleeves 52 to the upright frame member 30' supported on frame member 18". Clearance cavities 56 formed through the lower pelvic section 22' provide the clearance necessary for the attachment and movement of the axial traction member 50 as previously described.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. In a flexion-traction type lumbar traction table including a base which supports a stationary head-thoracic support section and a movable pelvic support section positioned on said base in spaced generally end-to-end relation to and being separate from said head-thoracic support section, the improvement comprising:

generally coextensive upper and lower pelvic sections connected together for sliding longitudinal translation therebetween and forming said pelvic support section;

a proximal end of said lower pelvic section pivotally connected to a frame of said base for pivotal movement only about a transverse flexion axis between a generally horizontal first position and a downwardly inclined second position of said lower pelvic section;

an elongated longitudinally extending axial traction member pivotally connected at one end thereof about a first transverse pivotal axis to said upper pelvic section adjacent to a distal end thereof, another end of said traction member pivotally connected to said frame about a second transverse pivotal axis, said second pivotal axis spaced beneath said flexion axis wherein said upper pelvic section is automatically slidably translated further from said proximal end of said lower pelvic section as said pelvic support section is manually pivoted from the first to the second position.

2. The improvement of claim 1, further comprising:

a traction handle connected to and upwardly extending from said lower pelvic section for enhanced manual positioning of said pelvic support section between said first and second positions.

3. The improvement of claim 2, wherein:

said traction handle is spaced evenly between side margins of, and in proximity to a distal end of, said lower pelvic section;

said traction handle extending upwardly through a clearance opening through said upper pelvic section to accommodate relative sliding movement of said upper pelvic section with respect to said lower pelvic section while being moved between said first and second positions.

4. A flexion-traction type lumbar traction table for supporting and treating a patient, comprising:

a base supporting a stationary head-thoracic support section and a movable pelvic support section positioned on said base in spaced generally end-to-end relation to and being separate from said head-thoracic support section;

generally coextensive upper and lower pelvic sections connected together for sliding longitudinal translation therebetween and forming said pelvic support section;

a proximal end of said lower pelvic section pivotally connected to a frame of said base for pivotal movement only about a transverse flexion axis between a generally horizontal first position and a downwardly inclined second position of said lower pelvic section;

an elongated longitudinally extending axial traction member pivotally connected at one end thereof about a first transverse pivotal axis to said upper pelvic section adjacent to a distal end thereof, another end of said traction member pivotally connected to said frame about a second transverse pivotal axis, said second pivotal axis spaced beneath said flexion axis wherein said upper pelvic section is automatically slidably translated further from said proximal end of said lower pelvic section as said pelvic support section is manually pivoted from the first to the second position.

5. The traction table of claim 4 further comprising:

a traction handle connected to and upwardly extending from said lower pelvic section for enhanced manual positioning of said pelvic support section between said first and second positions.

6. The traction table of claim 5, wherein:

said traction handle is spaced evenly between side margins of, and in proximity to a distal end of, said lower pelvic section;

said traction handle extending upwardly through a clearance opening through said upper pelvic section to accommodate relative sliding movement of said upper pelvic section with respect to said lower pelvic section while being moved between said first and second positions.

7. A flexion-traction type lumbar traction table for supporting and treating a patient, comprising:

a base supporting a stationary head-thoracic support section and a pelvic support section positioned on said base in spaced generally end-to-end relation to and being separate from said head-thoracic support section;

said pelvic support section being pivotally movable about an upright axis positioned centrally of side margins thereof and in proximity to a proximal end of said pelvic support section;

generally coextensive upper and lower pelvic sections connected together for sliding longitudinal translation therebetween and forming said pelvic support section;

a proximal end of said lower pelvic section connected to a frame of said base for pivotal movement about a horizontal transverse flexion axis for pivotal movement between a generally horizontal first position and a downwardly inclined second position of said pelvic support section;

an elongated longitudinally extending axial traction member pivotally connected at one end thereof to said upper pelvic section adjacent to a distal end thereof about a first transverse pivotal axis passing through or in very close proximity to said upper pelvic section, another end of said traction member pivotally connected to said frame about a second transverse pivotal axis, said second pivotal axis spaced beneath said flexion axis wherein said upper pelvic section is automatically slidably translated further from said proximal end of said lower pelvic section as said pelvic support section is manually pivoted from the first to the second position.

8. The traction table of claim 7, further comprising:

a traction handle connected to and upwardly extending from said lower pelvic section for enhanced manual positioning of said pelvic support section between said first and second positions.

9. The traction table of claim 8, wherein:

said traction handle is spaced evenly between side margins of, and in proximity to a distal end of, said lower pelvic section;

said traction handle extending upwardly through a clearance opening through said upper pelvic section to accommodate relative sliding movement of said upper pelvic section with respect to said lower pelvic section while being moved between said first and second positions.

* * * * *